US009538758B2

(12) United States Patent
Johannessen

(10) Patent No.: US 9,538,758 B2
(45) Date of Patent: Jan. 10, 2017

(54) METHOD OF COMBATTING SEA LICE

(75) Inventor: Baard Johannessen, Arendal (NO)

(73) Assignee: NETTFORSK AS, Arendal (NO)

( * ) Notice: Subject to any disclaimer, the term of this patent is extended or adjusted under 35 U.S.C. 154(b) by 431 days.

(21) Appl. No.: 12/669,089

(22) PCT Filed: Jul. 16, 2008

(86) PCT No.: PCT/GB2008/002444
§ 371 (c)(1),
(2), (4) Date: Mar. 2, 2010

(87) PCT Pub. No.: WO2009/010755
PCT Pub. Date: Jan. 22, 2009

(65) Prior Publication Data
US 2010/0184726 A1 Jul. 22, 2010

(30) Foreign Application Priority Data
Jul. 16, 2007 (GB) .................................. 0713790.4

(51) Int. Cl.
A01N 57/12 (2006.01)
A01N 43/90 (2006.01)
A01N 53/02 (2006.01)
A01N 53/00 (2006.01)

(52) U.S. Cl.
CPC .................................... *A01N 53/00* (2013.01)

(58) Field of Classification Search
IPC .......................................... A01N 57/12,43/90,
See application file for complete search history.

(56) References Cited

U.S. PATENT DOCUMENTS

| 4,210,642 | A | 7/1980 | Bock et al. |
| 4,882,873 | A | 11/1989 | Purnell |
| 5,096,895 | A | 3/1992 | Matthewson |
| 5,782,799 | A | 7/1998 | Jacobsen et al. |
| 5,866,152 | A | 2/1999 | Takebayashi et al. |
| 7,014,804 | B2 | 3/2006 | Johansen |
| 2012/0135962 | A1 | 5/2012 | Johannessen |

FOREIGN PATENT DOCUMENTS

| AU | 561106 B2 | 4/1987 |
| CA | 2020554 C | 1/1991 |
| CN | 1305716 A | 8/2001 |
| DE | 2932920 A1 | 4/1981 |
| EP | 0013582 A1 | 7/1980 |
| EP | 0279523 A1 | 8/1988 |
| GB | 1276703 A | 6/1972 |
| GB | 1581277 A | 12/1980 |
| GB | 2088718 A | 6/1982 |
| GB | 2099701 A | 12/1982 |
| GB | 2343627 A | 5/2000 |
| JP | 50058237 A | 5/1975 |
| JP | 62270516 | 11/1987 |
| JP | 06248293 | 9/1994 |
| WO | 9205764 A1 | 4/1992 |
| WO | 9216106 A1 | 10/1992 |
| WO | 01/48330 A1 | 7/2001 |
| WO | 02076213 A1 | 10/2002 |
| WO | 03092378 A1 | 11/2003 |
| WO | 2006111553 A1 | 10/2006 |
| WO | 2007131950 A2 | 11/2007 |
| WO | 2009010755 A2 | 1/2009 |

OTHER PUBLICATIONS

Grant; "Medicines for sea lice"; 2002; Pest Management Science; 58: 521-527.*
Grave; "Consumption of drugs for sea lice infestations in Norwegian fish farms: methods for assessment of treatment patterns and treatment rate"; 2004; Diseases of Aquatic Organisms; 60: 123-131.*
Roth (contributions to zoology 69(1/2) 109-118 (2000).*
Guillet, P. et al., Combined pyrethroid and carbamate 'two-in-one' treated mosquito nets: field efficacy against pyrethroid-resistant Anopheles gambiae and Culex quinquefasciatus, Medical and Veterinary Entomology, 2001, pp. 105-112, vol. 15, Blackwell Science Ltd.
Gunning, R. V. et al., Esterase Inhibitors Synergise the Toxicity of Pyrethroids in Australian Helicoverpa armigera (Hubner) (Lepidoptera: Noctuidae), Pesticide Biochemistry and Physiology, 1999, pp. 50-62, vol. 63, NSW Agriculture, Tamworth Centre for Crop Improvement.
Bruno, D. W. et al., Potential of carbaryl as a treatment for sea lice infestations of farmed Atlantic salmon, Council Meeting of the International Council for the Exploration of the Sea, 1989.
Schering-Plough Animal Health, Sea Lice Technical Monograph, 2002, The Animal Pharm Consulting Group.
Grant, Andrew N., "Medicines for sea lice", Pest Management Science, vol. 58, May 7, 2002, pp. 521-527.
Ahmad, M.; Saleem, M. A.; Sayyed, A.H., "Efficacy of insecticide mixtures against pyrethroidand organophosphate-resisant populations of Spodoptera litura (Lepidoptera: Noctuidae)", Pest Management Science, vol. 65, Dec. 2, 2008, pp. 266-274.
Ahmad, M., "Observed potentiation between pyrethroid and organophosphorus insecticides for the management of Spodoptera litura (Lepidoptera: Noctuidae)", Crop Protection, vol. 28, Dec. 13, 2008, pp. 264-268.
Vericore Ltd, Novartis Animal Vaccines Ltd., EXCIS treatment against sea-lice, Vetcare Veterinary Products, 2008, pp. 1-4.
Sigmund Sevatdal et al, Monooxygenase medicated pyrethroid detoxification in sea lice (Lepeophtheirus Salmonis), Pest Management Science, Aug. 2005, 61(8); 772-8.
Chris Wallace, Marine Harvest, Confidential Fax message to Stephen Macintyre, dated Jan. 13, 2004.
Baard Johannessen, Method of Combatting Human Head Lice, U.S. Appl. No. 12/669,110, filed Jan. 14, 2010, Art Unit 1629.
Sinniah et al., Pediculosis Among Rural School Children in Kelang et al., J. of the Royal Soc. of Health, vol. 104, No. 3, pp. 114, 115, 118, United Kingdom (1994).

(Continued)

Primary Examiner — Shirley V Gembeh
(74) Attorney, Agent, or Firm — Kagan Binder, PLLC

(57) ABSTRACT

The invention provides a method of treatment of farmed fish to combat infestation by multicellular ectoparasites with exoskeletons, which method comprises topically exposing farmed fish, especially salmon in sea cages, to a first and a second sea lice treatment agent, said first sea lice treatment agent being a carbamate or organophosphate and said second sea lice treatment agent being a pyrethroid or pyrethrin.

20 Claims, No Drawings

(56) References Cited

OTHER PUBLICATIONS

Kyle, Comparison of Phenotrin Shampoo et al., J. of the Royal Soc. of Health, vol. 110, No. 2, pp. 62-63, United Kingdom (1990).
Stenersen, Chemical Pesticides: Mode of Action and Toxicology, CRC Press, United States (2004).
Oxford Dictionary of Biochem. and Molecular Biology, p. 197, Oxford Univ. Press, 1997 (definition of "ectoparasite").
Oxford Dictionary of Biochem. and Molecular Biology, p. 197, Oxford Univ. Press, 1997 (definition of "insecticide").
The Role of B-Type Esterases in Conferring Insecticide Resistance in the Tobacco Whitefly, Bemisia Tabaci (Genn), Byrne et al., Pesticide Management Science, 56:867-874, Society of Chemical Industry, 2000.
Roth, Myron et al. "Field trials on the efficacy of the organophosphorus compound azamethiphos for the control of sea lice (Copepoda: Caligidae) infestations of farmed Atlantic salmon (*Salmo salar*)", Aquaculture 140: 217-239, United Kingdom (1995).
Martin, Thibaud et al. "Organophosphorus Insecticides Synergize Pyrethroids in the Resistant Strain of Cotton Bollworm, *Helicoverpa armigera*(Huber) (Lepidoptera: Noctuidae) from West Africa", Journal of Economic Entomology 96(2): 468-474, West Africa (2003).
Hamed, M. et al. "Toxicity of Different Insecticide Mixtures Against Cotton Bollworm, *Helicoverpa armigera*(Hub.) (Lepidoptera: Noctuidae)", Pakistan J. Zool., 38(1): 39-42, Pakistan (2006).
Bonnet, Julien et al. "Topical Applications of Pyrethroid and Organophosphate Mixtures Revealed Positive Interactions Against Pyrethroid-Resistant Anopheles Gambiae", Journal of American Mosquito Control Association, 20(4): 438-443, United States (2004).
O'Halloran, John et al. "First use in North America of azamethiphos to treat Atlantic salmon for sea lice infestation: Procedures and efficacy", Can. Vet. J. 37: 610-611, Canada (1996).
"Ecological effects of sea lice medicines in Scottish sea lochs", Scottish Association for Marine Science, Plymouth Marine Laboratory (2005).
Search Report dated Jul. 16, 2009 in connection with United Kingdom Patent Application No. GB0905165.7.
International Search Report and Written Opinion dated Oct. 25, 2010 in connection with International Patent Application No. PCT/GB2010/000569.
Sievers, Gerold et al. "Evaluation of the toxicity of 8 insecticides in Salmo salar and the in vitro effects against the Isopode parasite, Ceratothoa gaudichaudii", Aquaculture 134, Issue 1-2, pp. 9-16, United States (1995).
"Avoiding Resistance in Sea Lice", Integrated Sea Lice Management brochure (2005).
Jones, Kimberly N. et al. "Review of Common Therapeutic Options in the United States for the Treatment of Pediculosis Capitis", Therapeutic Options for Pediculosis Capitis, CID 2003, pp. 1355-1361.
Flinders, David C. et al. "Pediculosis and Scabies", American Family Physician, 69:2, Jan. 15, 2004, pp. 341-348.
Meinking, Terri L. et al. "Efficacy of a Reduced Application Time of Ovide Lotion (0.5% Malathion) Compared to Nix Creme Rinse (1% Permethrin) for the Treatment of Head Lice", Pharmacology and Therapeutics, Pediatric Dermatology, 21:6, 2004. pages 670-674.
Brand, Rhonda M. et al. "Decreasing malathion application time for lice treatment reduces transdermal absorption", International Journal of Pharmaceutics 301 (2005) pp. 48-53.
Store Norske Leksikon definitions of ectoparasites and parasitism, Nov. 29, 2012.
Caligus, Issue 6, Mar. 2000, 24 pages.
The Merck Veterinary Manual: A handbook of diagnosis and therapy for the veterinarian. Fifth Edition (1979) pp. 746-747 and 1560-1569.
The Merck Veterinary Manual. Tenth Edition (2010) pp. 832-833, 1632-1633, and 2352-2363.
Therapy Recommendation treatment against sea lice on salmon by the Norwegian Medicines Agency in Jun. 2000. Behandling mot lakselus i oppdrettsanlegg. SLK publication 2000:02, 43 pages.
Bielza, Pablo et al. "Synergism studies with binary mixtures of pyrethroid, carbamate and organophosphate insecticides on Frankliniella occidentalis (Pergrande)," Pest Management Science (63:84-89) 2007.
Audegond, L. et al. "Toxicologie Experimentale: Potentialisation de la toxicite de la deltamethrine par les inseciticdes organophosphores," Journal de Toxicologie Clinique et Experimentale, 1989. T. 9. No. 3, pp. 163-176.
Ahmad, Mushtaq. "Insecticide Resistance and Resistance Management: Potentiation/Antagonism of Pyrethroids with Organophosphate Insecticides in Memisia tabaci (Homoptera: Aleyrodidae)," J. Econ Entomol. 100 (3), 2007, pp. 886-893.
Burridge, Les et al. "Chemical Use in Salmon Aquaculture: A Review of Current Practices and Possible Environmental Effects," Mar. 20, 2008.
Denholm, Ian et al. "Analysis and management of resistance to chemotherapeutants in salmon lice, *Lepeophtheirus salmonis*(Copepoda: Caligidae)," Pest Management Science (58: 528-536) 2002.
Fallang, Anders et al. "Novel point mutation in the sodium channel gene of pyrethroid-resistant sea lice *Lepeophtheirus salmonis*(Crustacea: Copepoda)," Diseases of Aquatic Organisms, vol. 65, pp. 129-136, 2005.
Grave, K. et al. "Consumption of drugs for sea lice infestations in Norwegian fish farms: methods for assessment of treatment patterns and treatment rate," Diseases of Aquatic Organisms, vol. 60, pp. 123-131, 2004.
Sevatdal, Sigmund et al. "Determination of reduced sensitivity in sea lice (*Lepeophtheirus salmonis Kroyer*) against the pyrethroid deltamethrin using bioassays and probit modelling," Aquaculture 218 (2003), pp. 21-31.
Haya, K. et al. "A Review and Assessment of Environmental Risk of Chemicals Used for the Treatment of Sea Lice Infestations of Cultured Salmon," Hdb Env Chem vol. 5, Part M. 2005, pp. 305-340.
Sevatdal, Sigmund, "Sea lice resistance to chemotherapeutants: Bioassays as diagnostic tools for determination of sensitivity patterns in sea lice," Norwegian School of Veterinary Science in Oslo, Norway, 60 pages, 2004.

\* cited by examiner

METHOD OF COMBATTING SEA LICE

CROSS-REFERENCE TO RELATED APPLICATIONS

This application claims priority to International Application No. PCT/GB2008/002444, filed on Jul. 26, 2008, which in turn claims priority to United Kingdom Application Serial No. 0713790.4, filed on Jul. 16, 2007, the contents of which are both hereby incorporated by reference.

This invention relates to a method of topical treatment of living fish to combat multicellular ectoparasites with exoskeletons, especially ectoparasites of the crustacean order copepod, more particularly of the genera *Lepeophtheirus* (especially the salmon louse, *Lepeophtheirus salmonis*) and *Caligus* (especially *Caligus elongates*), to materials and to a treatment kit for use in that method.

Strange though it may seem, in aquaculture there is a major problem with the infestation of the cultured fish, for example salmon, with sea lice. Generally, the fish are treated with organophosphates, for example azamethiphos or dichlorvos, or pyrethroids, for example deltamethrin or cypermethrin which are known chemical sea lice treatments.

Chemical sea lice treatments which are currently available generally fall into three classes: organophosphates (e.g. malathion), carbamates (e.g. carbaryl), and pyrethroids (e.g. permethrin).

These sea lice treatment chemicals however have toxic effects. Concerns have long been expressed about organophosphate toxicity in particular, for example in relation to farm workers. Organophosphate poisoning does not require ingestion—cutaneous absorption can lead to signs of poisoning. Symptoms of organophosphate poisoning may include excessive excessive salivation, sweating, rhinorrhea, muscle twitching, weakness, tremor, incoordination, headache, dizziness, nausea, vomiting, abdominal cramps, diarrhea, respiratory depression, wheezing, blurred vision and more. Carbamates can cause adverse reactions such as sweating, vision blurring, incoordination and convulsions. Pyrethroids similarly can cause adverse reactions even on dermal exposure, such as excitory neurotoxicity, altered dopamine uptake, and dermatitis.

This is of particular concern not only in relation to the health of workers in the aquaculture industry and, obviously the health of the cultured fish, but also in relation to the release into the environment which almost inevitably occurs when non-juvenile fish, which are generally held in cages rather than tanks, are treated. We have found however that exposure to these chemical agents may be reduced by application of an organophosphate or carbamate and of a pyrethroid, optionally simultaneously, but preferably staggered and particularly preferably staggered in that order. Thus, the administration according to the invention is more concerned with reducing exposure to potentially toxic chemicals than with overcoming ectoparasite resistance to sea lice treatments.

Thus viewed from one aspect the invention provides a method of treatment of farmed fish to combat infestation by multicellular ectoparasites with exoskeletons, in particular sea lice, which method comprises topically exposing farmed fish, especially fish in cages, to a first and a second sea lice treatment agent, said first sea lice treatment agent being a carbamate or organophosphate and said second sea lice treatment agent being a pyrethroid or pyrethrin.

Viewed from another aspect the invention provides a pyrethroid or pyrethrin for use in treatment of fish by a method according to the present invention. Viewed from another aspect the invention provides an organophosphate or carbamate for use in treatment of fish by a method according to the present invention.

Viewed from a further aspect the invention provides a kit comprising in separate containers a first topical sea lice treatment agent composition containing a carbamate or organophosphate and a second topical sea lice treatment agent composition containing a pyrethroid or pyrethrin, and preferably also instructions for the use of said compositions in a method according to the present invention.

Viewed from a still further aspect the invention provides the use of a carbamate or organophosphate and a pyrethroid or pyrethrin for the preparation of topical sea lice treatment agent compositions for topical application to farmed fish to combat infestation by multicellular ectoparasites with exoskeletons.

The farmed fish treated according to the invention may be any fish susceptible of ectoparasite infestation. The fish however is especially preferably carp, tilapia, cod, halibut, or, most preferably a salmonid, such as trout or salmon, especially salmon.

Treatment of the farmed fish is topical in that the fish are introduced into an aqueous environment containing the sea lice treatment agent or caused to transit such an environment, or have the sea lice treatment agent introduced into the aqueous environment containing the fish. Thus for example, fish may be transferred into a tank for treatment or caused to pass from one holding zone, e.g. a tank or cage, into another through a conduit, e.g. a pipe or channel, containing the sea lice treatment agent. Alternatively, the sea lice treatment agent may be released into the cage, tank or pond containing the fish, optionally after surrounding the cage with an impervious barrier, e.g. a tarpaulin, to cause at least temporary retention of the sea lice treatment agent within the water in the cage. Particularly preferably, the sea lice treatment agent is released into the water within a cage, e.g. a sea cage, over an extended period so as to ensure exposure of the fish to the sea lice treatment agent before the agent is flushed out of the cage by the flow of surrounding water. Where the agent is to be released into a sea-cage, the sea-cage net will typically be raised to a depth of 2-2.5 meters and then surrounded by impervious tarpaulins to isolate the cage to be treated. Typically, the depth of enclosed water may be about 3 meters such that there will be some space (e.g. about 0.5-1 m) between the net bottom and the tarpaulin. The sea lice treatment agents may then be added to the prepared sea-cage at several locations to ensure maximum dispersion. Sequential treatment may be effected by sequential addition of different sea lice treatment agents or by sequential transfer through conduits or between tanks as discussed above.

The exposure to the sea lice treatment agents is desirably for a period of 10 to 100 minutes per agent, especially 15 to 60 minutes, especially about 20 to 40 minutes. Where treatment is sequential, it is desirably staggered by an intervening period of 10 minutes to 12 hours, especially at least 15 minutes, e.g. 15 minutes to 4 hours, more preferably 30 minutes to 3 hours, especially about 2 hours.

Particularly preferably, the fish are also treated (preferably pre-treated) with a monooxygenase inhibitor as a synergist for the pyrethroid/pyrethrin, e.g. piperonyl butoxide. This may be presented with the pyrethroid/pyrethrin treatment (e.g. in a mixture with the pyrethroid/pyrethrin), or prior to the pyrethroid/pyrethrin treatment. For example, this may be administered with the fish food, e.g. 12 hours to 60 hours, especially 24 to 48 hours, before exposure to the pyrethroid/pyrethrin.

The two sea lice treatment agent compositions may take any convenient topical application form, e.g. solution, dispersion, powder, etc. Since they will be diluted within the water in which the fish are present, their concentrations and formulations are not critical. Commercially available compositions may be used.

In an especially preferred embodiment, the first-applied composition is an organophosphate-containing solution, or a physiologically tolerable carbamate formulation, and the later applied composition is a pyrethroid-containing composition.

The organophosphate used according to the invention may be any organophosphate with ectoparasite killing effect (preferably with sea lice killing effect) which is physiologically tolerable on dermal application. Examples of such compounds include malathion, parathion, dichlorvos, azamethiphos, chlorpyrifos, chlorthion, trichlorphon, methyl parathion, and fenchlorphos. The use of azamethiphos or dichlorvos however is preferred. Where a carbamate is used, this may be any carbamate with ectoparasite killing effect (preferably with sea lice killing effect) which is physiologically tolerable on dermal application. One example of such a compound is carbaryl. The use of an organophosphate however is preferred.

For treatment of sea lice in particular, the organophosphate or carbamate is preferably present in the water to which the fish are exposed at a concentration of 5 to 1,000 ppb by wt., especially 10 to 500 ppb, particularly 20 to 300 ppb. For azamethiphos, the preferred concentration is 40 ppb, while for dichlorvos it is 200 ppb.

The pyrethroid or pyrethrin used according to the invention may be any pyrethroid or pyrethrin with ectoparasite killing effect (preferably with sea lice killing effect) which is physiologically tolerable on dermal application. Examples of such pyrethroid compounds, which are generally preferred relative to the pyrethrins, include permethrin, phenothrin, cypermethrin, pyrethrin and deltamethrin. The use of deltamethrin or cypermethrin however is preferred. The pyrethrins, if used, may for example be derived from natural sources such as the chrysanthemum plant. However, where pyrethrins are used, it is preferred also to use a synergist (as discussed above).

For treatment of sea lice in particular, the pyrethroid or pyrethrin is preferably present in the water to which the fish is exposed at a concentration of 0.5 to 50 ppb wt., especially 1 to 25 ppb, particularly 2 to 20 ppb. The preferred concentration for deltamethrin is 1 to 2 ppb, while that for cypermethrin is 5 to 10 ppb.

For treatment of other ectoparasites, the sea lice treatment agent concentrations may be adjusted appropriately.

The method of the invention may if necessary be repeated, e.g. after 7 to 10 days, but for a single case of infestation a single performance of the method will generally be sufficient.

One or both of the sea lice treatment agent compositions may advantageously contain a further sea lice treatment agent, e.g. selected from the chloronicotinyl (e.g. imidacloprid), phenylpyrazole (e.g. fipronil), oxadiazine (e.g. indoxacarb), pyrazole (eg chlorfenapyr), or organochlorine (e.g. lindane) classes.

While in the method of the invention it is most preferable to administer the pyrethroid/pyrethrin after the organophosphate/carbamate, administration in the reverse order can be beneficial and forms a further, though less preferred, aspect of the invention.

The invention claimed is:

1. A method of treating farmed fish infested with sea lice, the method comprising the following steps in order:
    releasing a first sea lice treatment agent to water within a cage, tank, or pond containing the fish, the first treatment agent comprising an organophosphate;
    retaining the first sea lice treatment agent within the cage, tank, or pond for a first period of time;
    releasing a second sea lice treatment agent to the water within the cage, tank, or pond, the second lice treatment agent comprising a pyrethroid or pyrethrin; and
    retaining the second sea lice treatment agent within the cage, tank, or pond for a second period of time,
    wherein the first period of time is 10 to 100 minutes, the second period of time is 10 to 100 minutes, about 5 ppb to about 1000 ppb of the first sea lice treatment agent is applied to the water, and about 1 ppb to about 25 ppb of the second sea lice treatment agent is applied to the water.

2. The method of claim 1, wherein the first lice treatment agent consists of an organophosphate.

3. The method of claim 1, wherein the second lice treatment agent is deltamethrin and about 1 ppb to about 2 ppb of the second lice treatment agent is applied to the water.

4. The method of claim 1, wherein the first sea lice treatment agent is flushed out of the cage before applying the second sea lice treatment agent.

5. The method of claim 1, wherein both the first and the second period of time are 15 to 60 minutes.

6. The method of claim 1, wherein the farmed fish are salmonids.

7. The method of claim 1, wherein exposure to the first sea lice treatment agent is effected up to 12 hours before exposure to the second sea lice treatment agent.

8. The method of claim 1, wherein the first sea lice treatment agent is selected from azamethiphos and the second sea lice treatment agent is selected from deltamethrin and cypermethrin.

9. The method of claim 1, wherein the sea lice treatments are released into water within a cage after surrounding the cage with an impervious barrier.

10. The method of claim 1, wherein about 5 ppb to about 20 ppb of the first lice treatment agent is applied to the water.

11. A method of treating farmed fish infested with sea lice, the method comprising the following steps in order:
    releasing a first sea lice treatment agent to water within a cage, tank, or pond containing the fish, the first treatment agent comprising a carbamate;
    retaining the first sea lice treatment agent within the cage, tank, or pond for a first period of time;
    releasing a second treatment agent to the water within the cage, tank, or pond, the second lice treatment agent comprising a pyrethroid or pyrethrin; and
    retaining the second sea lice treatment agent within the cage, tank, or pond for a second period of time,
    wherein the first period of time is 10 to 100 minutes, the second period of time is 10 to 100 minutes, 5 ppb to about 1000 ppb of the first lice treatment agent is applied to the water, and about 1 ppb to about 25 ppb of the second lice treatment agent is applied to the water.

12. The method of claim 11, wherein the first lice treatment agent consists of a carbamate.

13. The method of claim 11, wherein the second lice treatment agent is deltamethrin and about 1 ppb to about 2 ppb of the second lice treatment agent is applied to the water.

14. The method of claim 11, wherein the first sea lice treatment agent is flushed out of the cage before applying the second sea lice treatment agent.

15. The method of claim 11, wherein both the first and the second period of time are 15 to 60 minutes.

16. The method of claim 11, wherein the farmed fish are salmonids.

17. The method of claim 11, wherein exposure to the first sea lice treatment agent is effected up to 12 hours before exposure to the second sea lice treatment agent.

18. The method of claim 11, wherein the second sea lice treatment agent is selected from deltamethrin and cypermethrin.

19. The method of claim 11, wherein the sea lice treatments are released into water within a cage after surrounding the cage with an impervious barrier.

20. The method of claim 11, wherein about 5 ppb to about 20 ppb of the first lice treatment agent is applied to the water.

* * * * *